United States Patent [19]

Kambin

[11] Patent Number: 5,242,443
[45] Date of Patent: Sep. 7, 1993

[54] PERCUTANEOUS FIXATION OF VERTEBRAE

[75] Inventor: Parviz Kambin, Devon, Pa.

[73] Assignee: Smith & Nephew Dyonics, Inc., Andover, Mass.

[21] Appl. No.: 745,474

[22] Filed: Aug. 15, 1991

[51] Int. Cl.$^5$ .......................... A61B 17/56; A61F 2/44
[52] U.S. Cl. ...................................... 606/60; 606/61; 606/72; 623/17
[58] Field of Search ........................ 606/60, 61, 72, 73, 606/74, 75, 54, 57, 59, 105, 69–71; 623/16, 17

[56] References Cited

U.S. PATENT DOCUMENTS

| | | | |
|---|---|---|---|
| 1,960,892 | 5/1934 | Boever | 606/73 |
| 2,501,978 | 3/1950 | Wichman | 606/74 |
| 2,774,350 | 12/1956 | Cleveland | 606/61 |
| 3,693,616 | 9/1972 | Roaf | 606/61 |
| 3,848,601 | 11/1974 | Ma et al. | |
| 3,892,232 | 7/1975 | Neufeld | |
| 3,997,138 | 12/1976 | Crock | 606/61 |
| 4,341,206 | 7/1982 | Perrett et al. | |
| 4,488,543 | 12/1984 | Tornier | 606/65 |
| 4,545,374 | 10/1985 | Jacobson | |
| 4,573,448 | 3/1986 | Kambin | |
| 4,653,481 | 3/1987 | Howland | 606/61 |
| 4,678,459 | 7/1987 | Onik et al. | |
| 4,736,738 | 4/1988 | Lipovsek et al. | |
| 4,743,260 | 5/1988 | Burton | 606/61 |
| 4,805,602 | 2/1989 | Puno | 606/61 |
| 4,863,476 | 9/1989 | Shepperd | |
| 4,878,915 | 11/1989 | Brantigan | |
| 4,887,596 | 12/1989 | Sherman | 606/72 |
| 4,946,458 | 8/1990 | Harms | 606/72 |
| 5,015,255 | 5/1991 | Kuslich | |
| 5,019,081 | 5/1991 | Watanabe | |
| 5,026,373 | 6/1991 | Ray et al. | |
| 5,092,866 | 3/1992 | Breard et al. | |
| 5,092,868 | 3/1992 | Mehdian | |
| 5,092,893 | 3/1992 | Smith | |

OTHER PUBLICATIONS

P. Kambin, Arthoscopic Microdiscetomy, 1991, pp. 117–121.

H-H Leu et al, *Ibid*, pp. 123–125.
J. A. N. Shepperd, *Ibid*, pp. 127–129.
P. Kambin, J. Bone and Joint Therapy, 48-A, No. 4, 1966, pp. 779–782.
D. W. Guyer et al, Surgical Rounds for Orthopedics, Feb. 1989, pp. 17–21.
G. Karistrom et al, Cont. Orth., vol. 20, No. 3, Mar. 1990, pp. 285–300.
R. B. Cloward, Clin. Orth. Rel. Res., 193, Mar. 1985, pp. 5–15.
R. Roy-Camille, Clin. Orth. Rel. Res., 203, Feb. 1986, pp. 7–17.
R. Louis, *Ibid*, pp. 18–33.
A. D. Steffer et al, *Ibid*, pp. 45–53.

(List continued on next page.)

*Primary Examiner*—Michael A. Brown
*Attorney, Agent, or Firm*—Pravel, Hewitt, Kimball & Krieger

[57] ABSTRACT

A method for percutaneous fixation of a pair of vertebrae of a patient, which comprises posterolaterally entering the back of a patient percutaneously with a plurality of pedicle screws, screwing each pedicle screw into the medullary canal of the pedicles of adjacent thoracic and/or lumbar vertebrae or the pedicles of the L5 and S1 vertebrae, to a position where the proximal end thereof lies adjacent the fascia of the patient; inserting pedicle screw linkages under the skin of the back of the patient and detachably securing the linkage means to the proximal ends of the screws on the same side of the spinous processes of the vertebrae to restrict relative movement between the vertebrae. A kit is provided for percutaneous fixation of vertebrae of a patient, comprising a plurality of pedicle screws of different sizes, yet of a size to enable the distal end of each screw to be screwed into the medullary canal of a pedicle of a vertebra with the proximal end thereof lying adjacent the fascia of a patient.

21 Claims, 4 Drawing Sheets

U.S. PATENT DOCUMENTS

J. P. Kostnik, *Ibid*, pp. 103–115.

F. P. Magerl, *Ibid*, pp. 125–141.

E. P. Luque et al, Surgical Technique, "Interpendicular Segmental Fixation (ISF)".

P. R. Harrington, So. African J. Surgery, vol. 5, No. 1, Mar. 1967, pp. 7–12.

A. D. Steefee et al, Clin. Orth. Rel. Res., 227, 1988, pp. 99–102.

A. Schreiber et al, Percutaneous Nucleotomy, vol. 14, Apr. 1991, pp. 439–444.

A. Schreiber et al, Z. Orthop., 129, 1991, pp. 1–5.

R. Roy-Camille, Int. Orthopaedics, 13, 1989, pp. 81–87.

J. S. Thalgott et al, Spine, vol. 14, No. 1, 1989, pp. 91–93.

K. Zielke, Clin. Orth, Rel. Res. 203, Feb. 1986, pp. 151–158.

Simmons Plating System, Smith & Nephew Richards.

Rogozinski Spinal Rod System, Smith & Nephew Richards.

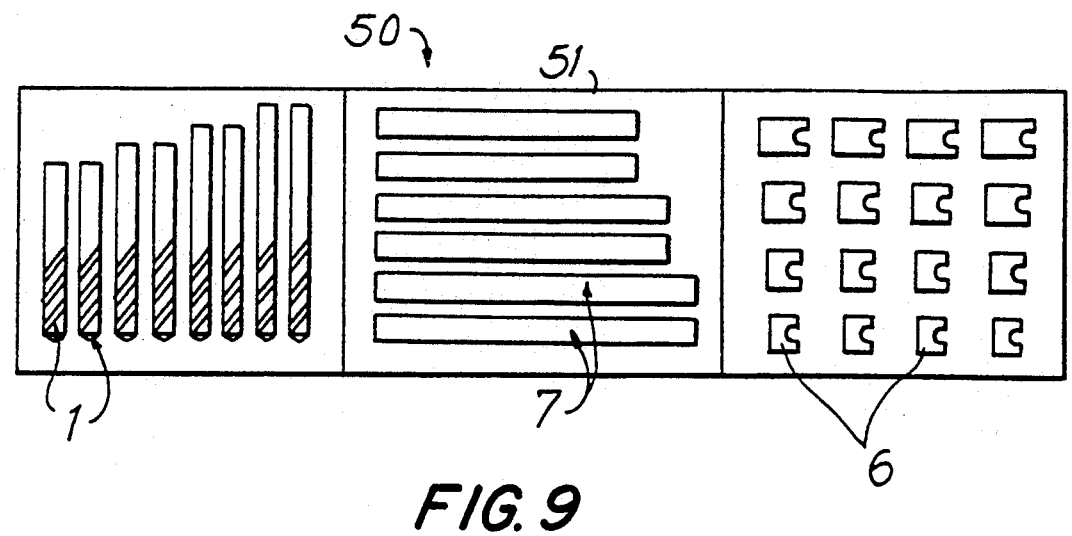
FIG. 9
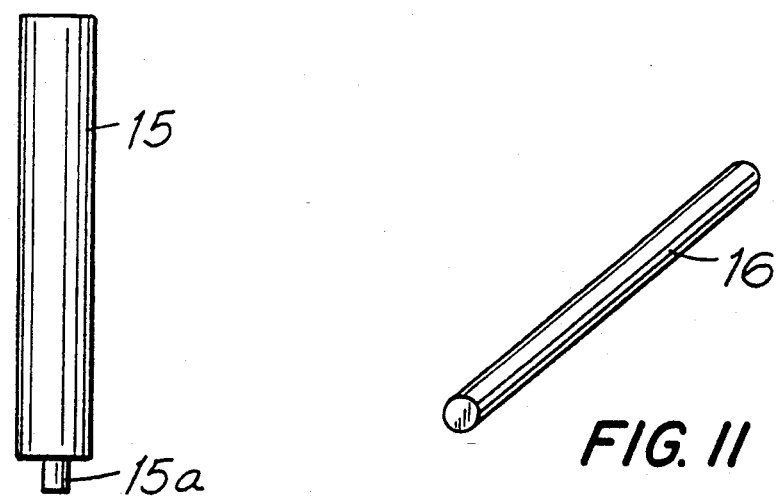
FIG. 10
FIG. 11

PERCUTANEOUS FIXATION OF VERTEBRAE

The present invention relates to percutaneous interbody fusion with subcutaneous internal fixators. More particularly, the present invention relates to percutaneous fixation of lumbar vertebrae by means of a minimally invasive technique.

The use of internal fixators for fixation of unstable fractures of the vertebrae is known. Also known is a system for internal fixation of vertebrae after the removal of one or more intervertebral discs. External fixation systems for the stabilization of thoracic and lumbar fractures have also been proposed.

The use of existing internal fixators requires a large incision in the back and dissection of the paraspinal muscles, which is a highly invasive procedure. If the internal fixators must be removed, a second major invasive procedure is required. Moreover, patients undergoing an internal fixation procedure require a lengthy rehabilitation, including reconditioning of the muscles.

The use of external fixators requires the patient to carry a fixation assembly on the surface of the back, which is difficult from a physical and psychological point of view for a majority of patients. Moreover, the rehabilitation of paraplegic patients with external fixators has proven to be difficult.

In addition, external fixators have portals in the skin which become sites for infection.

There is thus a need in the art for skeletal fixation that can be performed with minimal injury to the muscular ligamentous structures.

There is also a need in the art for a method of skeletal fixation whereby the extraction of the fixators is accomplished with minimal surgical intervention.

There is a further need in the art for a method of skeletal fixation which is acceptable both psychologically and cosmetically, and which minimizes infection.

The present invention provides a method for percutaneous fixation of vertebrae of a patient, which comprises posterolaterally entering the back of a patient percutaneously with a plurality of pedicle screws, screwing each pedicle screw into the medullary canal of the pedicles of adjacent thoracic and/or lumbar vertebrae or the pedicles of the L5 and S1 vertebrae, to a position where the proximal ends of the screws lie adjacent the fascia of the patient; inserting first and second pedicle screw linkage means under the skin of the back of the patient and detachably securing the linkage means to the proximal ends of said screws on the same side of the spinous processes of said vertebrae to restrict relative movement between the vertebrae.

As can be seen, the method of the present invention requires only a small incision to enable the surgeon to link the pedicle screws together. The fixators are located internally, thereby avoiding the disadvantages of external fixation. Since the subcutaneous fixators used in the present invention may be removed routinely after a period of rehabilitation, such as from 10 to 12 weeks, future MRI and CT visualization of the spinal canal and the lateral recesses are then possible. In contrast, the permanent implantation of internal fixators prevents the use of MRI and CT visualizations.

The present invention further provides a kit for percutaneous fixation of vertebrae of a patient, comprising a plurality of pedicle screws of different sizes, yet of a size to enable the distal end of each screw to be screwed into the medullary canal of each pedicle of a vertebra with the proximal end thereof lying adjacent the fascia of a patient. The kit may include a plurality of linkage means proportioned to lie under the skin of the patient and operable to detachably link together the proximal ends of the pedicle screws inserted into the pedicles of the vertebrae.

The present invention is illustrated in terms of its preferred embodiments in the accompanying drawings in which:

FIG. 9 is a plan view of a kit for carrying out the method of the present invention;

FIG. 10 is an elevational view of a tool used to carry out the method of the present invention; and FIG. 11 is a view in perspective of an alternative embodiment of the present invention.

Figure 1:
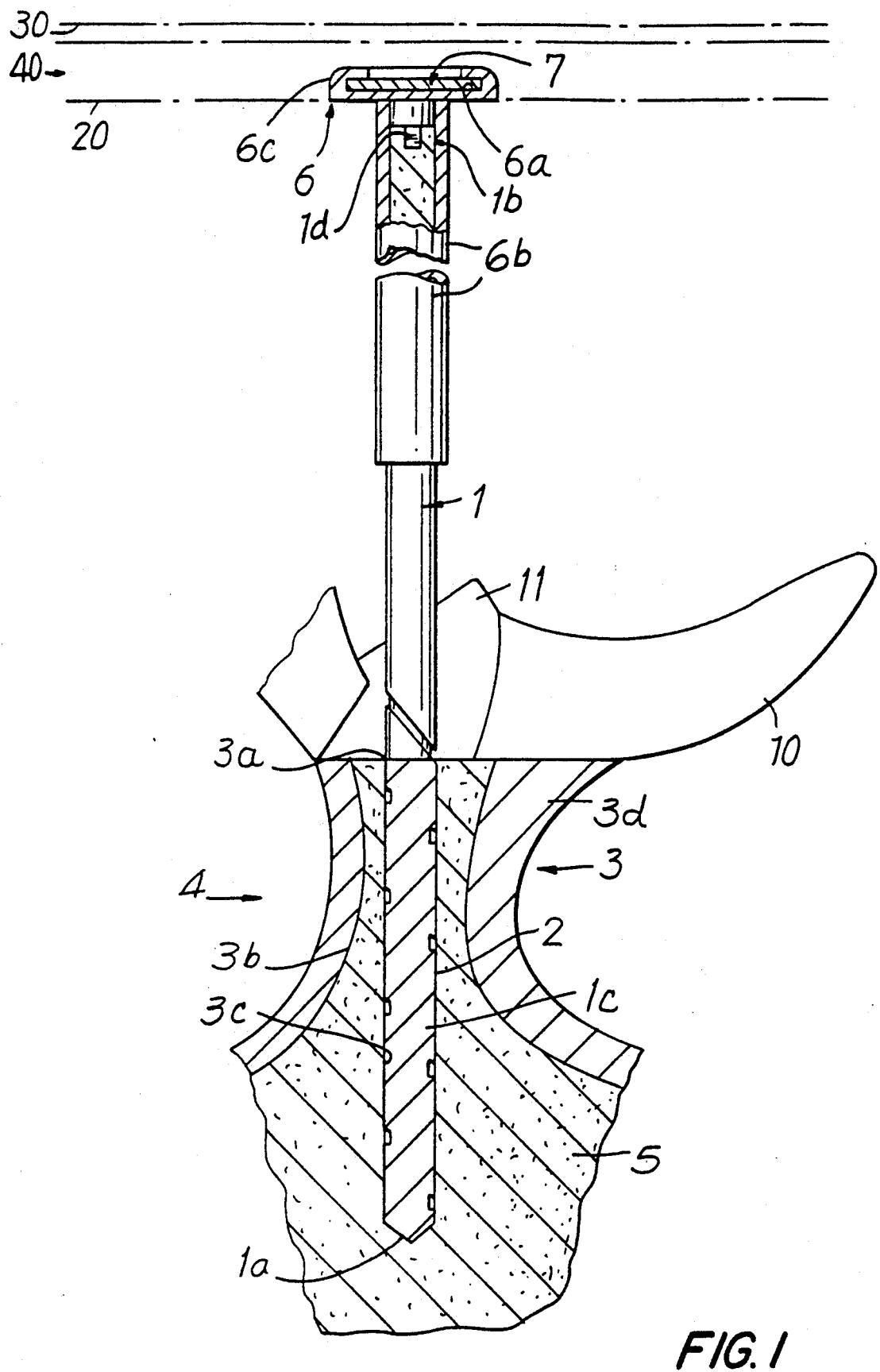
FIG. 1 is a schematic view, partly in section in enlarged scale, of one of the pedicles of a lumbar vertebra into which has been inserted a pedicle screw with a beam member detachably linked to the pedicle screw.

FIG. 1 schematically shows a pedicle screw 1 inserted into the medullary canal 2 of the pedicle 3 of a lumbar vertebra 4 of a patient. The distal end 1a of the pedicle screw 1 extends into the body 5 of the vertebra 4, while the proximal end 1b lies adjacent to the lumbar fascia 20 (shown in phantom line). Fastened to the proximal end 1b of pedicle screw 1 is an adaptor 6 having a slot 6a therein for receiving a beam member 7, here shown in the form of a plate. FIG. 1 shows the pedicle screw I inserted into the pedicle 3 situated to on side of the spinous process (not shown) of the vertebra 4. In the same manner, the pedicle (not shown) lying on the other side of the spinous process is also provided with a pedicle screw and an adaptor. The intervertebral disc t be removed lies between the vertebra 4 shown in FIG. 1 and a lumbar vertebra adjacent thereto (FIG. 2), which is also provided with pedicle screws inserted in the pedicles thereof, adaptors fastened to the proximal ends of the pedicle screws, and a beam member in the same manner as shown in FIG. 1.

Figure 2:
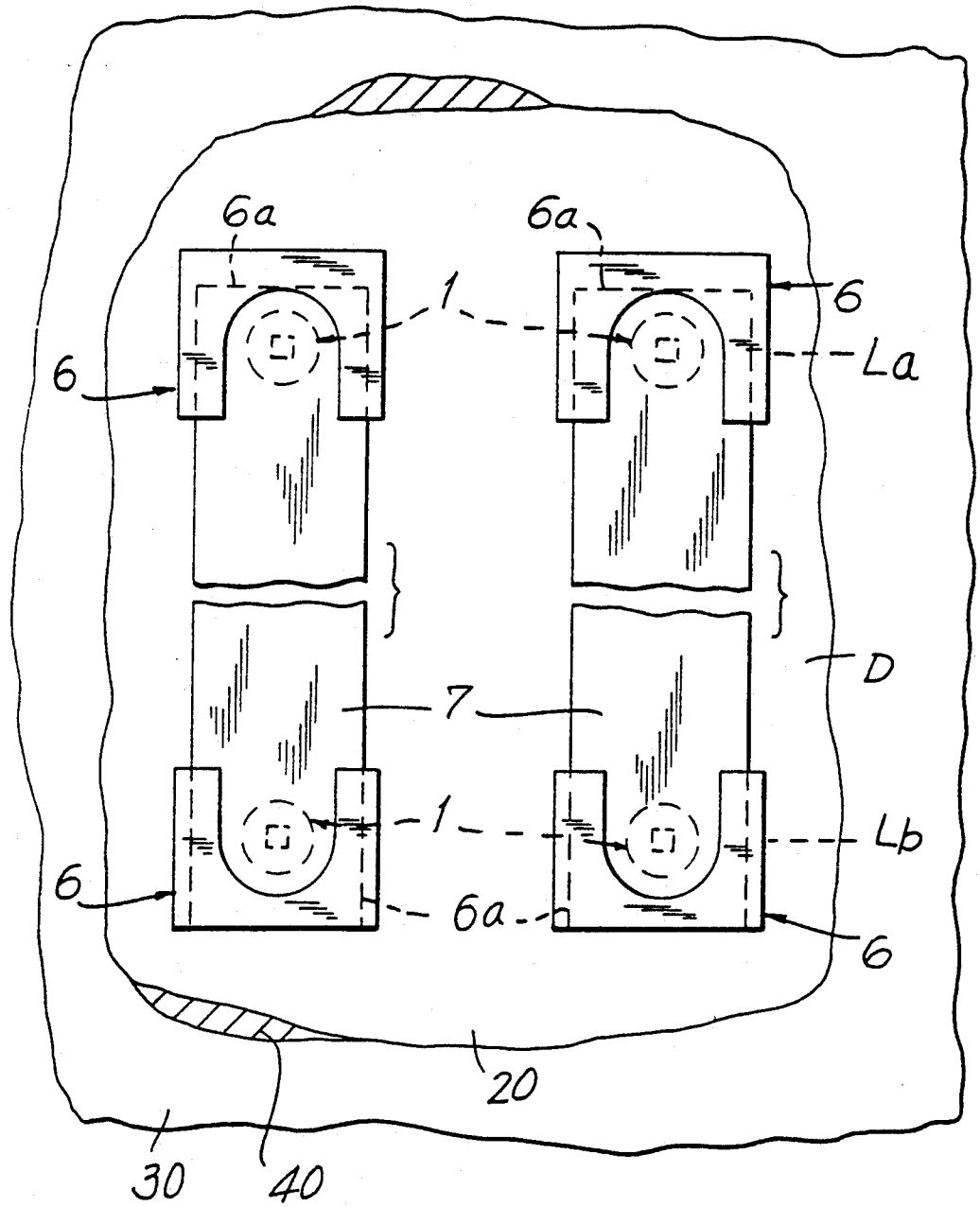
FIG. 2 is a schematic view, in enlarged scale, showing the subcutaneous fixation system of the present invention implanted in a patient.

FIG. 2 is a schematic view of the assembly of pedicle screws, adaptors and beam members of the invention, as viewed posteriorly with part of the skin 30 and subcutaneous tissue 40 of the patient removed for ease of illustration. Thus, pedicle screws 1 are held in the one pair of the pedicles (not shown) of lumbar vertebra L$a$, while the other pair of pedicle screws 1 is held in the pedicle of vertebra L$b$ immediately above or below lumbar vertebra L$a$. The intervertebral disc D to be removed is between lumbar vertebra L$a$ and L$b$ as schematically indicated. All of the adaptors 6 are preferably flush against the lumbar fascia 20 as shown in FIG. 1. Pedicle screws 1, adaptors 6 and beam members 7 are all made of biocompatible material, suitably stainless steel.

Figure 3:
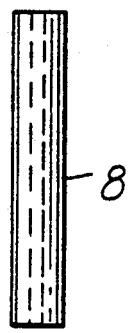
FIGS. 3–8 are elevational views of various instruments used to perform the surgical procedure of the present invention.
Figure 4:
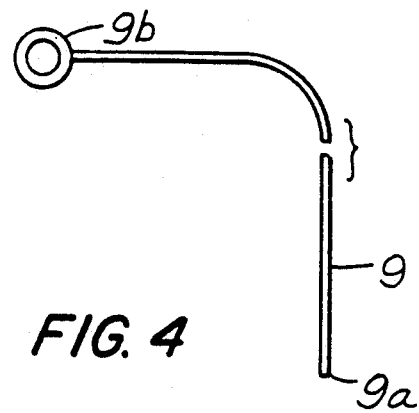
Figure 5:
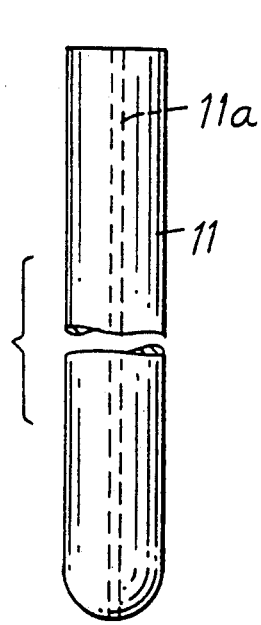
Figure 6:
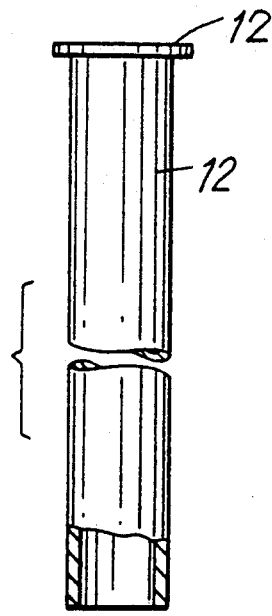

The surgical procedure for percutaneous fixation of lumbar vertebra of the invention may be carried out as follows. The patient is placed prone on a radiolucent table and frame (not shown). The C-arm of a conventional fluoroscope is positioned for anteroposterior visualization of the lumbar vertebrae and the table is tilted away from the C-arm to permit better localization of the pedicles. A cannulated tubular guide 8 (FIG. 3) is maneuvered by hand or by the flexible holder 9 (FIG. 4)

having its proximal end 9a secured to the table and carrying at its distal end a ring 9b for holding guide 8. The guide 8 is maneuvered with the holder 9 until the guide 8 is aligned with the longitudinal axis of the pedicle, after which the holder 9 is locked into place. When properly aligned, the guide 8 will appear by fluoroscopy as an opaque circle in the center of the pedicle. A guide wire (not shown), suitably of 2 mm outside diameter, is introduced into the guide 8 and is advanced through the skin of the patient's back, posterolaterally toward the pedicle 3. The guide wire is tapped with a mallet into the cortical bone at the junction of the base of the transverse process 10 (FIG. 1) and the proximal articular process 11. After removal of guide 8, a cannulated obturator 11 (FIG. 5) having a lumen 11a is placed over the guide wire and advanced through the skin of the patient's back to the pedicle 3, followed by placing an access cannula 12 (FIG. 6) over the obturator 11, and advancing the cannula 12 to the pedicle 3.

Figure 7:
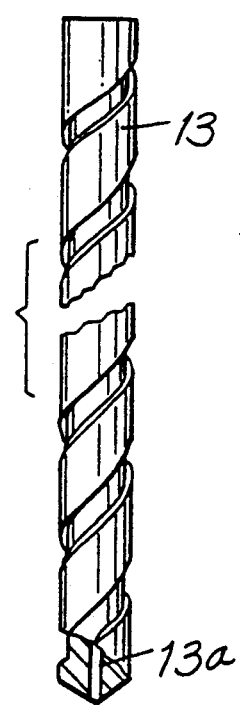
Figure 8:
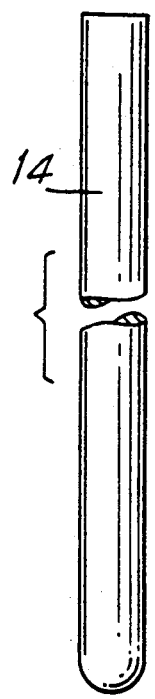

The obturator 11 is then removed, and a cannulated drill 13 having a lumen 13a (FIG. 7) is placed over the guide wire and advanced to the pedicle 3. By manually operating the drill 13, the opening of the cortex of the pedicle is enlarged to form an entrance 3a (FIG. 1) into the medullary canal 3b of the pedicle 3. The cannulated drill 13 is removed and a blunt end pedicle screw probe 14 (FIG. 8) is manually advanced into the medullary canal 3b with a twisting motion, to crush the cancellous bone of the medullary canal 3b thus creating a tunnel or bore 3c (FIG. 1) extending from the pedicle 3 into the vertebral body 5 (FIG. I). The probe 14 or a blunt end K-wire can be inserted into the bore 3c, the position and length of the probe or K-wire being checked by anteroposterior and lateral fluoroscopy.

If desired by the surgeon, the bore 3c may be tapped to receive the threads 1c of the pedicle screw 1. Alternatively, a self-tapping pedicle screw may be used. Before implanting the pedicle screw 1, the bore 3c may be inspected arthroscopically to make certain that the cortex 3d (FIG. 1) of the pedicle 3 has not been violated; if it has been, the surgeon may abort the procedure.

The length of the pedicle screw 1 to be used may be determined by the use of a K-wire. Thus, the K-wire can be used to measure the depth of bore 3c, and the distance between the bone and the lumbar fascia 20.

The appropriate pedicle screw 1 is selected from the kit 50 (FIG. 9) containing a plurality of pedicle screws 1, beam members 7 and adaptors 6 in a container 51. The pedicle screws 1 are all of a size to enable the distal end 1a of each screw 1 to be screwed into the medullary canal 3b of the pedicle 3 of a lumber vertebrae with the proximal end 1b thereof lying adjacent the lumbar fascia 20 of a patient, while the beam members 7 are proportioned to lie under the skin 30 of the patient and operate to detachably link together the proximal ends 1b of a pair of pedicle screws 1 (FIG. 2) inserted into the pedicles 3 of the lumbar vertebrae.

Generally, the pedicle screws 1 in kit 50 will be of different lengths and diameters. However, it is contemplated that the kit may contain pedicle screws 1 of different lengths and the same diameters. Moreover, while the beam members 7 may be of different lengths, all sized to be received in adaptors 6, some beam members 7 in the kit 51 may be much longer and will be cut to length by the surgeon. Adaptors 6 will comprise adaptors having a slot 6a open at one end and closed at the other, such as the upper adaptors 6 as viewed in FIG. 2, while others will have a slot 6a open at both ends, such as the lower adaptors 6 as viewed in FIG. 2.

The pedicle screw 1 selected is placed into the access cannula 12 and thence into the bore 3c. An allen wrench (not shown) may be inserted into the recess 1d (FIG. 1), to drive the pedicle screw 1 into the bore 3c. However, pedicle screw 1 may be provided with any suitable means for engaging a pedicle screw driver, such as a slot in screw 1 and a corresponding blade for the driver.

After pedicle screw 1 is implanted, an adaptor guide 15 (FIG. 10) having an outside diameter smaller than the inside diameter of the tubular body 6b is inserted through the access cannula 12 so that the projection 15a enters recess 1d (FIG. 1), after which the access cannula 12 is removed. An adaptor 6 is slid over the adaptor guide 15 and is screwed in place over the external threads on the proximal end 1b of screw 1, to the position shown in FIG. 1. All of the adaptors have an internally threaded tubular body 6b extending from a slotted cap 6c, the slot 6a lying in a plane perpendicular to the tubular body 6b. Adaptor guide 15 may also be used as a driver for the pedicle screws, for example by providing a slot (not shown) in the distal end of guide 15 to receive a cross-bar that serves as a handle.

After the pedicle screws are in place, the disc D is removed by percutaneous total discectomy. See, e.g., U.S. Pat. Nos. 4,573,448, 4,545,374 and 4,678,459. Bone grafts are then packed between the vertebral plates, and the vertebrae are aligned into their desired position by compression, extension and/or angulation using a wrench (not shown) or other tool that securely grasps the proximal ends 1b of the screws and/or the adaptors 6.

When the vertebrae are properly aligned, they are locked in place by inserting the beam members 7 into the adaptors 6 and, in turn, locking the beam members 7 in place. Thus, one end of the beam member 7 is received in an adaptor 6 having a slot 6a open at one end and closed at the other, such as the upper adaptors 6 shown in FIG. 2, while the other end is received in an adaptor 6 having a slot open at both ends, such as the lower adaptors 6 shown in FIG. 2.

To insert the beam member 7 into the adaptors 6, a small incision (not shown), may, if necessary, be made in the patient's back adjacent the adaptor 6 having a slot 6a having two open ends. The beam member 7 is inserted into the subcutaneous tissue 40 via the incision and advanced through adaptors 6 until the distal end of the beam member 7 contacts the closed end of adaptor 6. If necessary, the beam members 7 may be bent to allow the beam member 7 to be received by the adaptors 6. Each beam member 7 is locked in place in adaptors 6 by set screws (not shown) or by crimping the adaptors 6 and the ends of the beam member 7 or by any other suitable detachable locking means. The incision is then closed.

It is presently preferred that the adaptor cap 6 have a low profile, i.e. with a small thickness relative to its length and width. Preferably the cap 6c has a substantially flat top and flat underside as shown, but other configurations may be used as long as the cap 6 is proportioned to lie beneath the skin of the patient without substantially violating the skin and/or the lumbar fascia 20. Thus, if the beam members 7 are in the form of rods 16 (FIG. 11), the cap 6 may still be flat but a suitable cylindrical slot (not shown) will be used.

Suitably, the guide wire may be about 10 to 12 inches long while the cannulated obturator 11 may be about 6 to about 7 inches long and about 7 mm in diameter, with a lumen 11a sized to slide over the guide wire. The access cannula 12 may be about 5 to about 6 inches long with an inside diameter of about 7 mm. The cannulated drill 13 also has a lumen 13a sized to slide over the guide wire and will have an outside diameter somewhat smaller than the outside diameter of the pedicle screw.

The pedicle screw 1 may have an outside diameter of about 5 to about 6.5 mm and may suitably be from about 45 to about 70 mm in total length, with a distal portion 1c of about 20 to about 45 mm carrying a bone screw in thread form an the proximal portion being threaded to receive the adaptor 6. The tubular body 6b of the adaptor 6 may be about 15 to about 30 mm long, with a cap 6c of about 30×30 mm square and about 4 to 10 mm thick. The slot 6a must accommodate the beam member 7. Plates of about 5 to about 10 mm wide by about 35 to about 90 mm long are suitable, the thickness of the plates 7 being about 2 to about 5 mm. Rods 16 of about 5 to about 7 mm in diameter and 35 to about 90 mm long are also suitable. Anatomical Variations of a particular patient may require the use of different dimensions.

While the drawings show for convenience the fixation of only two vertebrae, it is to be understood that more than two vertebrae may be fixed. For example, when two intervertebral discs are to be removed, say between vertebrae L1, L2 and L3, pedicle screws 1 will be implanted in the pedicles of the three vertebrae. The pedicle screws rising from the L1 or L3 vertebra will carry an adaptor 6 having a slot closed at one end, while the other pedicle screws will carry an adaptor 6 having a slot open at both ends. A longer beam member 7 is then slid through the adaptors 6 and locked into place as described above. Moreover, the surgeon may elect to fix three vertebrae even if only one disc is to be removed.

While the present invention has been illustrated in the accompanying drawings in terms of the fixation of adjacent lumbar vertebrae, it is to be understood that the same procedures are followed for the fixation of adjacent thoracic vertebrae, of adjacent thoracic and lumbar vertebrae and of the L5 and S1 vertebrae. In each case, the procedure is effected percutaneously as described above. That is, the center of each pedicle to be implanted with a pedicle screw is located fluoroscopically, the pedicle screws are implanted percutaneously as described above and the proximal ends of the pedicle screws are linked together beneath the skin at or preferably flush with the muscle fascia as described above. If considered desirable by the surgeon, the beam members and/or the pedicle screws may be cross-linked together, such as by the use of 1.5 mm crosswires.

Moreover, while the kit 50 is illustrated as containing the screws, beam members and adaptors, the same or auxiliary kits may be provided with the instruments used to carry out the surgical procedure, such as the instruments shown in FIGS. 3-8 and 10.

I claim:

1. A method for percutaneous fixation of vertebrae of a patient, which comprises posterolaterally entering the back of a patient percutaneously with a plurality of pedicle screws, percutaneously screwing each pedicle screw into the medullary canal of the pedicles of adjacent thoracic and/or lumbar vertebrae or the pedicles of the L5 and S1 vertebrae, to a position where the proximal end thereof lies adjacent the fascia of the patient beneath the skin; inserting first and second pedicle screw linkage means between the skin and the lumbar fascia of the back of the patient and detachable securing said linkage means to said proximal ends of said screws on the same side of the spinous processes of said vertebrae to restrict relative movement between said vertebrae.

2. The method according to claim 1, wherein said pedicle screws are implanted in the pedicles of adjacent thoracic vertebrae.

3. The method according to claim 1, wherein said pedicle screws are implanted in the pedicles of adjacent lumbar vertebrae.

4. The method according to claim 1, wherein said pedicle screws are implanted in the pedicles of adjacent thoracic and lumbar vertebrae.

5. The method according to claim 1, wherein said pedicle screws are implanted in the pedicles of the L5 and S1 vertebrae.

6. A kit for percutaneous fixation of vertebrae of a patient, comprising a plurality of pedicle screws of different sizes, yet of a size to enable the distal end of each screw to be screwed into the medullary canal of a pedicle of a vertebra with the proximal end thereof lying adjacent the fascia of a patient, a plurality of linkage means proportioned to lie under the skin of the patient and operable to detachable link together the proximal ends of the said pedicle screws inserted into the pedicles of said vertebrae, said linkage means comprising a plurality of beam members being of different sizes and a plurality of adapter means for detachably securing said beam members thereto, said adapter means being of different sizes and detachable fastenable to said proximal ends of said pedicle screws.

7. The kit according to claim 6, wherein said pedicle screws are of different diameters.

8. The kit according to claim 1, wherein said pedicle screws have distal portions carrying bone screw threads of different lengths.

9. The kit according to claim 6, wherein said adaptor means comprise a slotted cap and a tubular body extending therefrom, said slot lying in a plane perpendicular to said tubular body, each of the slots being proportioned to receive a beam member, some of the caps having a slot open at both ends and others having a slot open at one end and closed at the other.

10. A method for percutaneous fixation of a pair of bar vertebrae of a patient, which comprises posterolaterally entering the back of a patient percutaneously and forming an opening in the cortical bone, of each said pair of lumbar vertebrae at the juncture of the base of the transverse process and the proximal articular process of said vertebrae, said openings providing entrances into the respective medullary canals of the pedicles supporting said processes; percutaneously screwing into each of said medullary canals a pedicle screw to a position where the proximal end thereof lies adjacent the lumbar fascia of the patient, providing for each pedicle screw an adaptor having a slotted cap and a tubular body extending therefrom, said slot lying in a plane perpendicular to said tubular body; fastening the tubular body onto the proximal end of each said pedicle screw such that said adaptor cap lies between the lumbar fascia and skin of said patient; sliding a beam member under the skin and into the slots of said caps; and detachably locking said beam members to said caps.

11. The method according to claim 10, wherein said vertebrae are aligned before insertion of said beam members, said beam members being locked in place to maintain said alignment.

12. The method according to claim 10, wherein the slot of one of said caps is open at both ends while the slot of the other said cap is open at one end and closed at the other, said beam member being slid through said slot of said one cap into said slot of said other cap.

13. The method according to claim 12, wherein a blunt end member is inserted in said access cannula and advanced into said medullary canal to crush cancellous bone therein and thereby form said medullary canal bore.

14. The method according to claim 13, wherein said pedicle screw is screwed into said medullary canal bore via said access cannula, and said access cannula is removed.

15. The method according to claim 14, wherein said adaptor is fastened onto said proximal end of said pedicle screw.

16. The method according to claim 15, wherein said adaptor is screwed in place onto said proximal end of said pedicle screw.

17. The method according to claim 15, wherein said adaptor cap is substantially flat and is fastened flush against the lumbar fascia of the patient.

18. The method according to claim 15, wherein the intervertebral disc between said vertebrae is removed and bone grafts are implaced before said beam members are inserted into each pair of associated adaptors and locked into place.

19. The method according to claim 13, wherein said pedicle screw has at its proximal end means for engaging a pedicle screw driver, said driver being introduced into said access cannula, said pedicle screw being screwed into said medullary canal bore by screw driver.

20. The method according to claim 10, wherein each said opening is formed by locating the position of said opening fluoroscopically, posterolaterally introducing a guide wire through the skin of the patient's back and advancing said guide wire to said location and into said critical bone at said junction; sliding a cannulated obturator over said guide wire and advancing said obturator to said junction; sliding an access cannula over said obturator and advancing said cannula to said juncture; removing said obturator; forming said opening with a pedicle cannulated drill means inserted in said access cannula over said guide wire and thereafter removing said guide wire and said drill means.

21. The method according to claim 10, wherein said beam member is a plate or rod.

* * * * *